United States Patent [19]

Wolfgang et al.

[11] 4,419,272

[45] Dec. 6, 1983

[54] CATALYSTS FOR THE PRODUCTION OF 2-CYANOPYRAZINE

[75] Inventors: Bergstein Wolfgang, Rodenbach; Heinz Friedrich, Hanau; Axel Kleemann, Hanau; Günther Prescher, Hanau; Helmut Beschke, Hanau, all of Fed. Rep. of Germany

[73] Assignee: Degussa AG, Frankfurt, Fed. Rep. of Germany

[21] Appl. No.: 351,404

[22] Filed: Feb. 23, 1982

[30] Foreign Application Priority Data

Feb. 28, 1981 [DE] Fed. Rep. of Germany ....... 3107756

[51] Int. Cl.³ .......................... B01J 21/16; B01J 23/16
[52] U.S. Cl. ...................................... 502/84; 502/324; 502/325; 502/337; 502/338; 502/350
[58] Field of Search ............................ 252/455 R, 456

[56] References Cited

U.S. PATENT DOCUMENTS

| 3,197,419 | 7/1965 | Callahan et al. | 252/456 |
| 3,259,652 | 7/1966 | Sachtler et al. | 252/456 X |
| 3,555,021 | 1/1971 | Beutel et al. | 260/250 |
| 3,923,819 | 12/1975 | Lüssling et al. | 252/456 X |
| 4,065,468 | 12/1977 | Grasselli et al. | 252/456 X |

Primary Examiner—Carl F. Dees

[57] ABSTRACT

For the catalytic reaction of 2-methylpyrazine with ammonia and oxygen to form 2-cyanopyrazine there are used compounds of the elements antimony, vanadium, and oxygen and at least one of the elements iron, copper, titanium, cobalt, manganese, and nickel, whereby the atomic ratio of antimony to vanadium is greater than 1 and which contain besides these compounds a lattice layer silicate and a highly dispersed silica. These catalysts are very selective and result in high yields and high space-time-yields.

9 Claims, No Drawings

CATALYSTS FOR THE PRODUCTION OF 2-CYANOPYRAZINE

CROSS REFERENCE TO RELATED APPLICATION

The catalyst of the present invention is also described as useful in producing 3-cyanopyridine in Helmut Beschke et al. application Ser. No. 351,402, filed Feb. 23, 1982, entitled "Catalysts For the Production of 3-Cyanopyridine".

BACKGROUND OF THE INVENTION

The invention is directed to a process for the production of 2-cyanopyrazine by catalytic reaction of 2-methylpyrazine with ammonia and oxygen at elevated temperature. It is particularly directed to catalysts for this purpose made of compounds of the elements antimony, vanadium, and oxygen, and at least one of the elements iron, copper, titanium, cobalt, manganese, and nickel, as well as the process for producing the catalysts.

There are known several processes for the production of 2-cyanopyrazine from 2-methylpyrazine through its reaction with ammonia and oxygen at elevated temperature in the gas phase. They differ through the reaction conditions and especially through the catalysts. Among the processes and catalysts only those are suitable for use on an industrial scale which show good selectivity and simultaneously result in high space-time-yields.

It is known to use as catalyst for the reaction of 2-methylpiperazine to form 2-cyanopyrazine compounds of the elements molybdenum, vanadium, and cobalt with oxygen, in a given case, on a carrier such as aluminum oxide (Beutel U.S. Pat. No. 3,555,021). This process also in the case of the reaction of 2-methylpyrazine to 2-cyanopyrazine only results in small amounts.

Besides it is known to use as catalyst for the reaction of 2-methylpyrazine to form 2-cyanopyrazine divanadium pentoxide in admixture with potassium sulfate on carriers such as aluminum oxide (Japanese publication No. 49-30382). This process results in only moderate yields and besides requires a large excess of ammonia.

Furthermore, it is known to use for the reaction of alkyl substituted heteroaromatics to form the corresponding CN-substituted compound catalysts which are produced from mixtures which contain antimony and vanadium in the atomic ratio of from 1.1:1 to 50:1 and at least one of the elements iron, copper, titanium, cobalt, manganese, and nickel and in a given case a carrier material and are prepared by heating to a temperature of 600° to 1100° C. in the presence of oxygen (German Pat. No. 2039497) and related Lüssling U.S. Pat. No. 3,923,819, the entire disclosure of which is hereby incorporated by reference and relied upon.

It is true that in this manner high space-time-yields are produced, however, the selectivity of the catalyst is unsatisfactory.

SUMMARY OF THE INVENTION

There have now been found catalysts for the reaction of 2-methylpyrazine with ammonia and oxygen to form 2-cyanopyrazine consisting of compounds of the elements antimony, vanadium, and oxygen and at least one of the elements iron, copper, titanium, cobalt, manganese, and nickel whereby the atomic ratio of antimony to vanadium is greater than 1, which are characterized by containing in addition to these compounds a lattice layer silicate and highly dispersed silica and have a BET surface area of 5 to 50 m$^2$/g, a macropore volume of 0.1 to 0.8 cm$^3$/g and an average pore radius of 1 to $8 \times 10^{-7}$ cm. These catalysts show an excellent selectivity and give good yields and good space-time-yields. They are outstandingly suited for use on an industrial scale. Especially advantageous are catalysts which contain antimony, vanadium, and titanium.

For the production of the catalyst of the invention there are used antimony and vanadium as well as the elements iron, copper, titanium, cobalt, manganese, and nickel suitably as compounds with oxygen, in the elemental form or as compounds which can be converted into compounds with oxygen, such as ammonium salts of oxygen acids, or nitrates.

The proportions are so chosen that in the catalysts the atomic portion of antimony is greater than that of vanadium. The atomic ratio of antimony to vanadium is suitably between 1.1 to 1 and 50 to 1, preferably between 1.1 to 1 and 25 to 1. As atomic ratio of antimony to iron, cobalt, copper, manganese, and nickel, individually or collectively, there is used 2 to 1 up to 20 to 1, preferably 3 to 1 up to 10 to 1. However, the atomic portion of iron, cobalt, copper, manganese, and nickel, individually and collectively, should no exceed the portion of vanadium. As atomic ratio of antimony to titanium there are suited 1 to 3 to 8 to 1, preferably 1 to 2 up to 4 to 1.

There is added to the so composed catalyst materials of the invention a mixture of a lattice layer silicate and highly dispersed silica so that in the catalysts their portion is about 10 to 60 weight percent, preferably 20 to 40 weight percent. The ratio of lattice layer silicate to highly dispersed silica in parts by weight is about 20 to 1 to 0.25 to 1, preferably 10 to 1 to 1 to 1.

Lattice layer silicates occurring in nature for use in the invention generally require a pretreatment. The silicate is finely powdered and, suitably under continuous movement, for example, in a rotary tubular furnace or fluidized bed furnace, heated to a temperature between 900° and 1200° C. The heating time depends on the type of lattice layer silicate, the temperature and the type of furnace. In most cases the material is held at a temperature within the range mentioned for at least one hour but not over 10 hours. Preferably there is used as the lattice layer silicate montmorillonite and for this the treatment time is from 4 to 6 hours at 975° to 1050° C.

The highly dispersed silica can be obtained in any desired manner, for example, by pyrolysis of silicon compounds, e.g. silicon tetrachloride, or trichlorosilane or by precipitation from solution of silicon compounds, e.g. sodium silicate. Suitably it has a BET surface area of about 50 to 500 m$^2$/g, preferably from 100 to 300 m$^2$/g.

For the production of the catalysts of the invention the starting materials are intensively mixed in the finest possible distributed form. It has proven advantageously hereby to add water and in a given case to introduce one or more of the substances as a solution or suspension in water. There are added to the mixtures molding aids as well as pore formers in the most finely divided form possible and if necessary additional liquids, also in a given case carrier materials.

As molding aids and pore formers there are used the materials customarily employed for this purpose, as molding aid for example, graphite, stearic acid, or polyethylene powder, as pore former for example, urea, ammonium carbonate, or carbohydrates such as saccharides, e.g. sugar, starch, or cellulose. The molding aid suitably is present in an amount of 1 to 15 weight percent, preferably 2 to 10 weight percent of the catalyst mixture and the pore former is suitably present in an amount of 0.1 to 50 weight percent, preferably 0.5 to 40 weight percent.

Besides water there are chiefly used water miscible organic solvents, especially polyhydric alcohols such as glycol or glycerine or also mixtures of these liquids. The content of liquid of the catalyst mixture is suitably about 10 to 35 weight percent, preferably 15 to 30 weight percent.

The preferred methods of operation for the preparation of the catalyst mixtures are either first to insert antimony or antimony trioxide into nitric acid and to treat at the boiling temperature and then to add divanadium pentoxide or ammonium vanadate and the other elements, these being added as the nitrate or the titanium as titanium dioxide, as well as the lattice layer silicate and the highly dispersed silica and to again treat the entire mixture at the boiling temperature or to add these materials simultaneously to nitric acid and to treat at the boiling temperature, finally, in a given case after neutralization of the acid, to bring the mixtures to dryness and to heat to a temperature of about 280° to 300° C. The molding aid and the pore former are added to the thus treated mixtures and, if necessary, after grinding the mixture to particles below 0.5 mm, the liquid added.

The catalyst mixtures are then pressed to briquettes whose size is suitably between about 1 and 8 mm. For this purpose there are used customary devices, for example, tabletting machines or extruders. Especially suited are granulate forming machines, especially cog wheel granulate forming machines.

The briquettes are treated in the presence of oxygen at a temperature between about 350° and 900° C., preferably between 500° and 800° C.

The finished catalysts generally have a BET surface area of about 5 to 50 m$^2$/g, a macropore volume of about 0.1 to 0.8 cm$^3$/g, and an average pore radius of about 1 to 8×10$^{-7}$ cm. Its bulk density is about 0.9 to 1.4 kg/l. According to their shape and size they are used in fixed bed or in fluid bed reactors.

The reaction of the 2-methylpyrazine with ammonia and oxygen to form 2-cyanopyrazine takes place in customary manner in the gas phase. There is suitable a wide range of reaction conditions. The reaction is chiefly carried out without the use of pressure or under slight excess pressure up to about 3 bar at a temperature between about 270° and 460° C., preferably at a temperature between 310° and 390° C. It is advantageous to supply the necessary oxygen as air. The ratio of 2-methylpyrazine to ammonia, oxygen, or air and in a given case steam can be chosen within wide limits. Generally it is suitable to use per mole of 2-methylpyrazine, about 3 to 8 moles, preferably 4 to 7 moles of ammonia, about 30 to 70 moles, preferably 45 to 65 moles of air. Per liter of bulk volume of catalyst per hour there are suitably fed into the reactor about 1 to 4.5 moles preferably 2.0 to 4.0 moles of 2-methylpyrazine.

In the examples all parts and percent are by weight unless otherwise indicated.

The compositions can comprise, consist essentially of the stated materials and the process can comprise, consist essentially of, or consist of the recited steps with such materials.

DETAILED DESCRIPTION

Example 1

23.3 kg of antimony trioxide, 4.7 kg of ammonium metavanadate, 12.8 kg of titanium dioxide, 11.7 kg of montmorillonite, and 5.8 kg of highly dispersed silica having a surface area of 200 m$^2$/g were suspended in 140 liters of water. Then there were added 16.4 liters of 54% nitric acid. The mixture was slowly heated to the boiling temperature, treated with 7 liters of water and held for 2 hours at the boiling temperature, then adjusted to a pH of 4.6 with ammonia, cooled, dried on a roller drier, heated in a tubular rotary drier to 300° C. and ground in a spike mill to a particle size below 0.5 mm. 4500 grams of the thus prepared catalyst mixture was intensively mixed with 225 grams of graphite and 1700 grams of a 20% aqueous urea solution and then shaped to extruded briquettes having a diameter of 3 mm. The briquettes were heated in the air stream and held hereby for 15 hours at 120° C., 2 hours at 550° C., 1 hour at 650° C., and 3 hours at 770° C. The bulk density of the catalyst was 1.05 kg/l, the BET surface area 18 m$^2$/g, the macropore volume 0.28 cm$^3$/g and the average pore radius 2.7×10$^{-7}$ cm.

84 grams of the catalyst were filled into a reaction tube having a clear width of 21 mm and a length of 550 mm. In homogeneous flow there were fed into the tube hourly 0.29 moles of 2-methylpyrazine with a gas mixture which contained per mole of 2-methylpyrazine 3.8 moles of ammonia and 48 moles of air. The gas mixture was supplied preheated to the reaction tube. The tube was heated by a salt melt which was held at 366° C. Upon leaving the reaction tube the gases were washed with water. In the course of 8 hours on the average 88% of the 2-methylpyrazine employed reacted as determined by continuous gas chromatography. The yield of 2-cyanopyrazine on the average, based on the 2-methylpyrazine employed was 80 mole % and the space-time-yield 290 g/lXh.

Example 2

The same catalyst and procedure were used as in Example 1 but the salt bath temperature was held at 380° C. and there were fed in a gas mixture which contained per mole of 2-methylpyrazine 3.7 moles of ammonia and 46.6 moles of air. In the course of 8 hours the average reaction was 97%, the yield of 2-cyanopyrazine 82 mole % and the space-time-yield 306 g/lXh.

Example 3

The same catalyst and procedure were used in Example 1 but the salt melt was held at 380° C. and there was fed in hourly 0.23 mole of 2-methylpyrazine with a gas mixture that contained 4.7 moles of ammonia and 59.8 moles of air per mole of 2-methylpyrazine. In the course of 8 hours the average reaction was 99%, the yield of 2-cyanopyrazine 85 mole % and the space-time-yield 245 g/lXh.

The entire disclosure of German priority application No. P 3107756.0 is hereby incorporated by reference.

What is claimed is:

1. A composition suitable to catalyze the reaction of 2-methylpyrazine with ammonia and oxygen to form 2-cyanopyrazine consisting essentially of the elements antimony, vanadium and oxygen and additionally at least one of the elements iron, copper, titanium, cobalt, manganese, and nickel where the atomic ratio of antimony to vanadium is greater than 1 and which contains in addition to these compounds a lattice layer silicate and highly dispersed silica and which has a BET surface area of 5 to 50 m$^2$/g, a macropore volume of 0.1 to 0.8 cm$^3$/g, and an average pore radius of 1 to 8×10$^{-7}$ cm.

2. A catalyst according to claim 1 wherein the atomic ratio of antimony to vanadium is between 1.1 to 1 and 50:1, the atomic ratio of antimony to said additional element when it is iron, cobalt, copper, manganese, or nickel is between 2 to 1 and 20 to 1 with the proviso that the atomic portion of said additional element does not exceed that of vanadium and when the additional element is titanium, the atomic ratio of antimony to titanium is between 1 to 3 and 8 to 1, the mixture of lattice layer silicate and highly dispersed silica is about 10 to 60 weight %, the ratio of lattice layer silicate to highly dispersed silica is between about 20 to 1 and 0.25 to 1 parts by weight and the silica has a BET surface area of about 50 to 500 m$^2$/g.

3. A catalyst according to claim 2 wherein the atomic ratio of antimony to vanadium is between 1.1 and 25 to 1, the atomic ratio of antimony to said additional element when it is iron, cobalt, copper, manganese, or nickel is between 3 to 1 and 10 to 1 and when the additional element is titanium the atomic ratio of antimony to titanium is between 1 to 2 and 4 to 1, the mixture of lattice layer silicate and highly dispersed silicate is 20 to 40 weight percent, the ratio of lattice layer silicate to highly dispersed silica is between 10 and 1 and 1 to 1 and the highly dispersed silica has a BET surface area of about 100 to 300 m$^2$/g.

4. A catalyst according to claim 3 wherein the lattice layer silicate is montmorillonite.

5. A catalyst according to claim 2 wherein the lattice layer silicate is montmorillonite.

6. A catalyst according to claim 5 wherein the additional element is titanium.

7. A catalyst according to claim 4 wherein the additional element is titanium.

8. A catalyst according to claim 3 wherein the additional element is titanium.

9. A catalyst according to claim 2 wherein the additional element is titanium.

* * * * *

UNITED STATES PATENT AND TRADEMARK OFFICE
CERTIFICATE OF CORRECTION

PATENT NO. : 4,419,272

DATED : December 6, 1983

INVENTOR(S) : BERGSTEIN ET AL

It is certified that error appears in the above-identified patent and that said Letters Patent is hereby corrected as shown below:

Title page:

Change the name of the first inventor from "Bergstein Wolfgang" to --Wolfgang Bergstein--.

UNITED STATES PATENT AND TRADEMARK OFFICE
CERTIFICATE OF CORRECTION

PATENT NO. : 4,419,272

DATED : December 6, 1983

INVENTOR(S) : BERGSTEIN ET AL

It is certified that error appears in the above-identified patent and that said Letters Patent is hereby corrected as shown below:

Claim 10 should be added as follows:

--10. A process for the production of the composition of claim 1 comprising heating in the presence of oxygen to a temperature between 350 and 900°C a mixture of antimony and vanadium or their oxides or their compounds capable of being converted to their oxides in a mole ratio of antimony to vanadium of greater than 1 and at least oneof the elements iron, copper, titanium, cobalt, manganese, and nickel, or their oxides or compounds capable of being converted to the oxide, a lattice layer silicate and highly dispersed silica.--

Signed and Sealed this

Fifth Day of February 1985

[SEAL]

Attest:

DONALD J. QUIGG

Attesting Officer

Acting Commissioner of Patents and Trademarks